(12) United States Patent
Law et al.

(10) Patent No.: US 6,808,929 B1
(45) Date of Patent: Oct. 26, 2004

(54) DEVICE AND METHOD FOR PHYSIOCHEMICAL MEASUREMENTS

(75) Inventors: Brian Law, Cheshire (GB); Bryan J A Miller, Bedfordshire (GB); Christopher M Turner, Middlesex (GB); John E A Shaw, Middlesex (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/763,826

(22) PCT Filed: Oct. 11, 1999

(86) PCT No.: PCT/GB99/03370

§ 371 (c)(1), (2), (4) Date: Apr. 12, 2001

(87) PCT Pub. No.: WO00/22428

PCT Pub. Date: Apr. 20, 2000

(30) Foreign Application Priority Data

Oct. 13, 1998 (GB) .............................................. 9822185

(51) Int. Cl.$^7$ ................................................. G01N 21/62
(52) U.S. Cl. ....................... 436/52; 436/172; 436/177; 436/180; 422/80; 422/81; 422/100
(58) Field of Search ................................ 436/172, 177, 436/180, 52; 422/81, 82, 99, 100, 101, 103

(56) References Cited

U.S. PATENT DOCUMENTS 5,643,738 A  7/1997 Zanzucchi et al.
5,716,852 A  2/1998 Yager et al.
2001/0048637 A1 * 12/2001 Weigl et al. ................. 366/341

FOREIGN PATENT DOCUMENTS

| WO | 96/04547 | 2/1996 |
| WO | 96/12541 | 5/1996 |
| WO | 97/00442 | 1/1997 |
| WO | 98/00231 | 1/1998 |
| WO | 98/09161 | 3/1998 |

OTHER PUBLICATIONS

Cowen, Simon, "Small is beautiful," Chemistry & Industry, pp. 792–793 (1998).

Manz et al, "Electroosmotic pumping and . . . ," Micromech. Microeng., vol. 4, pp. 257–265 (1994).

* cited by examiner

Primary Examiner—Lyle A. Alexander
(74) Attorney, Agent, or Firm—Nixon & Vanderhye

(57) ABSTRACT

The invention relates to a microfabricated device for use in measuring the physical properties of compounds, where the properties measured using such devices are those which involve partitioning of the compound between two phases, measuring partition coefficients, distribution coefficients, acid-base dissociation constants, solubility and vapour pressure. The device comprises a microfabricated conduit, in which two fluids flow creating at least two phases between which the compound may partition, and a detector for measuring the amount of compound in each or both fluids.

16 Claims, 4 Drawing Sheets

DEVICE AND METHOD FOR PHYSIOCHEMICAL MEASUREMENTS

The invention relates to a microfabricated device for use in measuring the physical properties of compound samples, where the properties measured using such devices are those which involve partitioning of the compound between two phases, measuring partition coefficients, distribution coefficients, acid-base dissociation constants, solubility and vapour pressure.

BACKGROUND OF THE INVENTION

The biologically active compound, for example a pharmaceutical or agrochemical compound, depends on a range of physicochemical and biopharinaceutical attributes of that compound which governs the bioavailability of the compound in the target and non-target species or tissue or organism or at a target or non-target enzyme or molecule. In order to accelerate the rate of discovery of such molecules, there is currently considerable interest in the measurement of such properties for large numbers of compounds very early in the discovery process so that these factors may be used to influence future decisions on which molecules to synthesis as potential candidates for drug or agrochemical research programs.

Synthetic techniques such as multiple parallel synthesis (MPS) and combinatorial chemistry provide relatively small sample sizes, for example in the microgram range. The limited sample sizes currently produced are not large enough to supply more than a few tests within the drug discovery process before the supply is exhausted. Therefore, resynthesis may be required in order to restock the chemical library.

Candidate compounds of potential interest may therefore only be available in relatively small amounts i.e. <1 mg. There is therefore a strong need for methods that can be applied to large numbers of compounds without requiring proportionately more resources and which are capable of dealing with small sample weights. Conventional methods often employ complex separation steps which are time-consuming. Although these can be automated, the serial nature of the analysis i.e. one sample at a time, still effectively limits the throughput.

Microfabrication techniques are generally known in the art using tools developed by the semiconductor industry to miniaturise electronics, it is possible to fabricate intricate fluid systems with channel sizes as small as a micron. These devices can be mass-produced inexpensively and are expected to soon be in widespread use for certain simple analytical tests. See, e.g., Ramsey, J. M. et al. (1995), "Microfabricated chemical measurement Systems," Nature Medicine 1:1093–1096; and Harrison, D. J. et al (1993), "Micromachining a miniaturized capillary electrophoresis-based chemical analysis system on a chip," Science 261:895–897. In addition devices have been proposed for preparative, analytical and diagnostic methods which bring two streams of fluid in laminar flow together which allows molecules to diffuse from one stream to the next, examples are proposed in WO9612541, WO9700442 and U.S. Pat. No. 5716852.

Miniaturisation of laboratory techniques is not a simple matter of reducing their size. At small scales different effects become important, rendering some processes inefficient and others useless. It is difficult to replicate smaller versions of some devices because of material or process limitations. For these reasons it is necessary to develop new methods for performing common laboratory task on the microscale.

DESCRIPTION OF THE INVENTION

We have found that it is possible to measure in a microfabricated device physical properties such as the physicochemical, biopharmaceutical or environmental properties of a compound, or material containing a compound, if it is allowed sufficient time to partition between two phases where at least one phase is then analysed to provide the information for determining the physical property.

Biopharmaceutical properties include, for example, protein binding, in vitro metabolism, passive and active membrane transport. Environmental properties include, for example, soil binding, soil metabolism, water:air distribution and leaching. Physicochemical properties include, for example, partition coefficients, distribution coefficients, acid-base dissociation constants, solubility and vapour pressure.

Accordingly, we present as a first feature of the invention a method for the measurement of one or more physical property of a compound in a microfabricated device which method comprises;
(i) providing through an internal surface defining a conduit of the microfabricated device a flow of a fluid and present within the fluid is a compound;
(ii) moving the fluid through the conduit to bring it into contact with an agent to allow any partitioning of the compound through a partition interface formed between the fluid and the agent;
(iii) measuring the amount of compound or a derivative of the compound present during and/or after partitioning between the fluid and the agent in either the fluid or the agent, or both.

We present as a further feature of the invention a system for the determination of at least one physical property of a compound which comprises:
(i) a microfabricated device having an internal surface defining a conduit through which fluid may flow, compound being present in the fluid.
(ii) the conduit containing an agent to which the fluid is brought into contact:
(i) a detector for measuring the amount of compound or compound derivative present within the fluid or the agent or both; wherein partitioning of the compound through a partition interface formed between the fluid and the agent and presence of compound in either the fluid or the agent or both is measured to determine the physical property.

In this disclosure, the term "agent" may be any substance into which the compound may partition. The exact agent used will depend upon the physical property being measured. The agent may, for example, be a fluid or solid or semi-solid material. The agent may consist of or contain materials including chemical or biological reagents, membrane(s), cell(s), cell fragment(s), and mixtures of such materials. Preferably the agent is a fluid. Fluid agent may contain dissolved or suspended materials including chemical or biological reagents, membrane(s), cell(s), cell fragment (s), and mixtures of such materials. Preferably the agent is a fluid.

In this disclosure, the term "fluid" is significant as it is the fluids that define the nature of the phases between which the compound will, if able, partition. The fluid may itself be the compound, with or without other fluids, or may be a solvent for the compound. The fluid may be a gas, vapour, liquid or supercritical fluid (gas or liquid). The fluid may also be a mixture of different fluids. The fluid will be chosen according to the physical property being measured. Preferably the fluid is a liquid.

In this disclosure the term "partition interface" means a point or points at which the fluid and the agent contact each other and a surface forming boundary is made through which the compound must pass for partition to occur. Alterbatively, "partition interface" means a point or points at which a further third fluid is present which itself forms a boundary between the fluid and the agent.

In this disclosure, the term "microfabricated" includes devices capable of being fabricated on polymeric, ceramic, glass, silicon wafers (preferably monocrystalline silicon), or other suitable materials available to those practising the art of microfabrication and having the feature of sizes and geometries producible by microfabrication techniques. Microfabrication techniques include such methods as, photoligraphy, LIGA, thermoplastic micropattern La transfer, resin based microcasting, micromolding in capillaries (MIMIC), wet isotropic and anisotropic etching, laser assisted chemical etching (LACE), and reactive ion etching (RIE), or other techniques known within the art of microfabrication. In the case of silicon microfabrication, larger wafers will accommodate a plurality of the devices of this invention in a plurality of configurations. A few standard wafer sizes are 3" (7.5 cm), 4" (10 cm), 6" (15 cm), and 8" (20 cm). Application of the principles presented herein using new and emerging microfabrication methods is within the scope and intent of the invention. Microfabricated devices are created through innovative combinations of three essential manufacturing processes: (1) photolithography, the optical process of creating microscopic patterns (2) etching, the process that removes substrate material and (3) deposition, the process whereby materials with a specific function can be coated onto to surface of the substrate.

By "partitioning" we mean that the compound is allowed to move, if able, from the fluid to the agent. This partitioning may be allowed to reach equilibrium before measurements are taken, or measurements may be taken prior to equilibrium being reached. However, it will be appreciated that it may be advantageous in terms of time, as described below with reference to diffusion path lengths, to take one or more measurements before partition equilibrium and deduce the physical property on the basis of extrapolation, or on the basis of a calibration curve.

Preferably, where the agent is a fluid, the "second fluid", then this may be any fluid as defined above into which the compound may partition and is a fluid which will form a phase interface when in contact with the first fluid. The exact fluid used will depend upon the physical property being measured and may be, for example, a fluid which is partially miscible or non-miscible with the first liquid, a solvent, a gas, or any other fluid as defined above in the definition of "fluids".

The fluid agent and the fluid within which is carried the compound are preferably non miscible. For immiscble fluids the partitioning interface is defined by the physical interface maintained between the two fluids.

Subject to some restrictions the fluid agent and the fluid within which is carried the compound may be miscible. The two fluids may be miscible where a boundary region between the two fluids can be defined and maintained as by parallel laminar flow and where the diffusive transfer of compound through and between the fluids is significantly faster than the mixing of the fluids or transfer of dissolved or suspended material from the fluid agent to the fluid containing compound. This may be achieved where material suspended or dissolved in the fluid agent consists of macromolecules, colloid particles, cells, or cell fragments which have very low diffusion rates compared with the compound.

In this disclosure, the term "compound" refers to any substance of biological or chemical origin. Derivatives of the compound are those where the compound has been altered in some way by exposure to the agent, for example, solvated, metabolised, ionised, reduced, oxidised, hydrolysed or dissolved.

In this disclosure the term "non-miscible" means that the two fluids (where at least one fluid is a liquid or a supercritical fluid) do not mix but could partially dissolve in the other, for example, water/octanol.

We present as a feature of the invention a method for the measurement of one or more physical property of a compound in a microfabricated device which comprises;
(i) providing through an internal surface defining a conduit of the microfabricated device a flow of fluid in which is present the compound;
(ii) bringing the flow of fluid into contact with a second fluid within the conduit for a sufficient period for any possible partitioning of the compound through a partition interface formed between the two fluids to occur;
(iii) measuring the amount of compound or derivative of the compound present after partitioning in either the fluid or the second fluid, or both.

We present as a further feature of the invention a method for the measurement of one or more physical property of a compound in a microfabricated device which method comprises;
(i) providing through an internal surface defining a conduit of the microfabricated device two liquids;
(ii) the first liquid contains a compound, the second liquid is non-miscible with the first liquid;
(iii) bringing the two liquids together, preferably in parallel laminar flow, for a sufficient period for any possible partitioning of the compound through a partition interface formed between the two fluids to occur;
iv) measuring the amount of compound or derivative of the compound in the first liquid, the second fluid, or both.

In an alternative feature of the invention the first and second fluids are flowed along first and second conduits which converge, contact and then run parallel to one another with one or more restricted openings between the conduits thus forming a contacting conduit within which at the opening(s) contact is established between the two fluids. Parallel laminar flow is maintained for each fluid in their respective portions of the contacting conduit and such transfer of compound through the opening(s) between the portions of contacting conduit occurs as is consistent with possible partitioning of the compound between the fluids. Conduits may diverge from the contacting region separating the two fluids. This structure indicated diagramatically in FIG. 4 has advantages for maintaining stable contact between to flows of immiscible fluids.

The term parallel laminar flow means stable flow of the liquid through the conduit, there being no areas of turbulence. Therefore the presence of compound or compound derivative in the second liquid is entirely due to the ability of the compound to partition between the first liquid and the second liquid, i.e. its physical properties. See FIG. 4.

The term parallel laminar flow means that stable flow of fluid exists through a conduit with no regions of turbulence. Laminar flow is consistent with the low Reynolds number flow conditions which generally apply for low to moderate rate flows of liquids through channels of microengineered dimensions. Where contact between the fluids is established under parallel lamianr flow conditions, the presence of compound or deivative is entirely due to the ability of the compound to diffuse to and from the interface between the two fluids and to partition across the interface. By ensuring that diffusion distances across the conduits are sufficiently short to allow rapid diffusive transfer to and from the interface, conditions are established to allow the partition to proceed speedily to equilibrium. Measurements fluid flow ratios and of compound concentration in one or both fluids then allows calculation of the desired physical property. Measurements of concentration at multiple points along the conduits allows progress towards equilibrium to be monitored and flow rates to be selected so as to ensure that fluid contact time is sufficient for equilibrium to be substantially achieved. See FIG. 4.

Typically, for liquids the conditions for parallel laminar flow and rapid diffusive transfer of compound are met where the width of each portion of the contacting conduit is of the order of 100 $\mu$m or less. Preferably the microfabricated conduits which contain the contacting flows have a constant width and smooth internal surfaces.

The fluids may be propelled by means of a mechanical pump, by syringe drive, by applying a vacuum or pressure to one end of the channel, by gravity flow or by electro-osmosis. A preferred method is electro-osmosis, which may conveniently be achieved by the microfabrication of electrodes at the ends of the conduit, the voltages between electrodes being controlled conveniently externally to achieve the desired fluid movements. The fluids may be moved at variable rates in accordance with the method chosen. Each compound may be moved in the fluids creating the two phases to allow partition to occur during a fixed time period for each compound to provide information on the ranking of the compounds in a qualitative analysis rather than a quantitative measurement of the physical property.

We present as a further feature of the invention a method for the measurement of one or more physical property of a compound in a microfabricated device which method comprises;

(i) providing through an internal surface defining a conduit of the microfabricated device two moving fluids;
(ii) the first fluid contains compound;
(ii) the second fluid is non-miscible with the first fluid;
(iii) the two fluids moving together in the microfabricated conduit in contact with each other to allow a phase interface between the two fluids to form and allowing any possible partitioning of the compound from the first fluid to the second fluid to occur;
iv) measuring the amount of compound or derivative of the compound in the first fluid and/or the second fluid.

Due to the smaller quantities of fluid and sample which are used, diffusional distances within the fluid can be dramatically lowered allowing for equilibrium to be reached efficiently without the need for convective or advective mixing. However movement of the fluids through the conduit may be usefully employed to enhance or control mixing rates by taking into account possible advective mixing which may be caused by drag with the surface of the conduit.

Different compounds will reach the point of partition equilibrium at different rates, this is known as the rate of partition. The rate of partition of a sample may be affected by many different factors such as chemical kinetic factors and transport of dissolved material in the solvent by convective, advective, or diffusive processes. Within microfabricated conduits it is possible to limit convective or advective and in particular turbulent fluid transport so that diffusion may be the dominant mode of transport of the compound through the fluid. Where diffusive transfer is the limiting factor, the partition rate is related to the length of the path through which the compound molecules diffuse and the geometry of the fluid body in the conduit. Diffusive transfer rates will generally be inversely related to the square of the path length.

Typically diffusion coefficients (D) of samples of the size range of interest (MW of a few hundred) will be around $5 \times 10^{-6}$ cm$^2$s$^{-2}$, in a liquid, and have diffusive transfer times (t) across a path length (L) which may be derived from expressions of the type $Dt/L^2=0.01$ to 1 second, where $Dt/L^2=0.01$ approximates to a diffusion front reaching a distance across L from source plane, and $Dt/L^2=1$ corresponds to near completion of the diffusive process (concentration gradient across L being nearly eliminated). Approximate times for reaching diffusive equilibration ($Dt/L^2=1$) at different path lengths (L), in which the dissolved compound must travel, based on $D=5 \times 10^{-6}$ cm$^2$s$^{-1}$ are:

| | |
|---|---|
| L = 10 $\mu$m | t = 0.2 sec |
| L = 100 $\mu$m | t = 20 sec |
| L = 1 mm | t = 0.5 hours |
| L = 1 cm | t = 55 hours |

About 50% of the diffusive transfer will occur in about a tenth of the above times. Based on the above, the condition for relatively rapid equilibration (~<100 seconds) by diffusion alone can be met where the distance L across the liquid from a partition interface, generally a conduit width, is not greater than 100 $\mu$m and flow rates set to allow contact times between portions of first and second fluids of ~100 seconds or greater. This has impact on liquid volume, depending on geometry of the device, and especially the contact conduit length and widths, i.e. preferably fluid volumes in the contact conduit region at any time will be in the range 1 nl to 1 $\mu$l, and preferably in the range 10 nl to 100 nl. Larger volumes of the two fluids may be used by continuing the flow of first and second fluids through the contact region for any desired time.

For relatively rapid equilibration to occur, the diffusion path lengths typically encountered impose limitations on the dimensions of the fluid bodies and the enclosing microfabricated conduits in the contact region. For example we have found that where the fluids are liquids, the longest fluid dimension perpendicular to the contact interface should be in a range from 1 mm to 1 $\mu$m and preferably in a range from 100 $\mu$m to 1 $\mu$m. It will be appreciated that the corresponding length for the fluid, when it is a gas, could be significantly larger due to the faster rate of diffusion. Typically gaseous diffusion coefficients are of the order of 0.1 cm$^2$s$^{-1}$ and therefore diffusion lengths, and corresponding conduit widths, could be in the range 3 cm to 100 $\mu$m, preferably in the range 5 mm to 500 $\mu$m.

The conduit may be any shape in cross section, preferably it is round or elliptical with a smooth internal surface.

The consequent limitation on fluid path length can however be readily removed if the liquid is mixed by convective/advective processes within the device and this is a further feature of the invention. Movement of a portion of fluid along a conduit causes recirculation within that protion of fluid and thus transferring any compound present in the fluid from the ends of the fluid portion into the interior of the fluid portion. In addition changing the geometry of the liquid may greatly improve diffusion rates by shortening the diffusion path length, compare FIGS. 1 and 2 where a larger volume of liquid could be used in FIG. 2 than FIG. 1 and still only a reasonable diffusion time in both is needed to reach partition equilibrium.

Typical amounts of compound which may be used in this device range from 1 ng to 1 mg. Typical volumes of fluid used in this device range from 1 nl to 0.1 ml, the minimum liquid volume corresponds to a 100 μm side cube, depending upon whether the fluid is a liquid or a gas.

The conduit may be any shape in cross section, preferably it is round or rectangular with a smooth internal finish.

Limitations on fluid path length imposed by diffusive transfer can be readily removed if the liquid is mixed by convective/advective processes within the device and this is a further feature of the invention. In addition changing the geometry of the liquid may greatly improve diffusion rates by shortening path length. Where first and second fluids are brought into contact as sequential lengths of fluid or flows flowing along a conduit, recirculatory advective movement of fluid within flows induced by slug movement conveys material to and from the slug end interfaces at rates which can be very significantly higher than those for diffusion. In particular the recirculatory fluid transport of material within the fluid of a slug will proceed at rates linearly related to the rate of movement of the slug along a conduit and transport times from the slug end surface to the interior will increase linearly with distance from the interface rather than with the square of distance as for diffusion.

Advective mixing within flows of fluid may be achieved both by flow in a single direction and also by reciprocating flow where the direction of movement of the flows along a conduit is periodically reversed. Use of reciprocating flow allows a more compact device construction as the length of conduit required to carry out the partitioning transfer is reduced.

Section of slug flow with first and second fluids may be separated by slugs of a third fluid chosen to be immiscible with either and preferably both first and second fluids and also chosen not to provide significant partion capacity for the compound or other materials dissolved or suspended in the first and second fluids. Where the first and second fluids are liquids or supercitical fluids, the third fluid may conveniently be a gas.

Within a slug diffusion rates perpendicular to the axis of flow will be related to the distance from axis to the confining walls of the conduit and thus to half the conduit width. This allows either faster diffusive transport for the same conduit width compared to that for diffusion between parallel contacting conduits, or allows the use of wider conduits without gross increase in diffusion times.

FIG. 1 represents the movement of immiscible fluid flows along a conduit with material transfer between adjacent flows. Such transfer based on sequential flows of first and second fluids can only be applied where those fluids are immiscible as it relies on surface tension effects to maintain the interfaces and prevent transfer of material between the fluids by advective flow.

In addition to the use of adjacent flows of first and second fluids in a simple conduit, the method can be extended so that partion can be carried out using adjacent flows in parallel conduits with restricted opening between the conduits. The first and second fluids flow in first and second contacting conduits with a third fluid separating flows of first or second fluid or both. This arrangement shown in FIG. 2 has the advantage of providing increased contact area between the first and second fluids whilst providing the advective mixing associated with movement and relatively short diffusion lengths.

Preferably the two fluids are brought together so that the phase interface is created at the point at which the two fluids contact each other and is formed in the conduit so the phase interface is approximately at 90° to the direction of flow of fluid—see FIG. 1, for example. Alternatively the phase barrier is approximately in the same plane to the direction of flow of fluid—see FIG. 2, for example.

Since both fluids are moving this allows serial analysis of samples in the same conduit in a continuous manner. By multiplying the number of conduits serial experiments may be performed in parallel to significantly further improve productivity.

When performing serial analysis in the same conduit it is important to allow a gap between the introduction of the first set of two fluids to prevent contamination by the second set of two fluids. A barrier plug may be inserted between each batch of two fluids. This barrier plug may simply be a gap in the introduction of the fluids, or an adiitional fluid or solid, into which compound cannot partition. It will be appreciated that by reference to two fluids we mean that two different fluids are inserted but that each fluid may be inserted more than once. For example fluid 1 may be inserted first, then fluid two and then fluid 1 so that two phase interfaces are created between the first and second fluids one either side of the second fluid—see FIG. 1.

In the invention the detection and measurement of the compound or derivative of the compound may be achieved either "on" the device or "off" the device or a combination of both. Suitable methods for determination using an on or off-device include potentiometry, conductiometry, mass spectrometry or methods of chromatography such as: capillary electrophoresis, high performance liquid chromatography (HPLC) or capillary electro chromatography with a variety of detection methods such as ultra violet (UV) or mass spectrometry (MS) Alternatively the chromatographic separation could be carried out on-device with detection such as UV or MS being carried out off the device. The attachment of an off-device detector to a microfluidic systems has been demonstrated in Bings N. et al. Proceedings of the μTAS'98 Workshop, Kluwer Academic Publishers, 141.

In the case of off-device detectors, a suitable interface to the measuring equipment will be required. In the case of mass spectrometry, suitable interfaces have already been described in Xue-Qifeng, Dunayevskiy-Yuri-M, Foret-Frantisek, Karger-Barry-L. Rapid Commun Mass Spectrom, VOL: 11 (12), P: 1253–1256, 1997. Further developments in device interfacing may be expected and are hereby incorporated into the device and methods of the invention.

It also may be desirable to measure using on or off-device methods the amount or concentration of compound present in the inlet stream prior to partitioning.

Connections with fluid reservoirs external to the device may be made in accordance with Mourlas N. J. et al. Proceedings of the μTAS'98 Workshop, Kluwer Academic Publishers 27, and references cited therein.

Devices may be conceived where the measurement of more than one property is made simultaneously (e.g. partition coefficient measurements using several different solvents or with the same solvent at several pHs to measure pKa) and conversely where the same measurement is made on several different compounds.

Methods for the manufacture of the devices of the invention may be adapted from those described in W09612541, W09700442 and U.S. Pat. No. 5,716,852.

BRIEF DESCRIPTION OF THE DRAWINGS

The invention is illustrated by the following non-limiting diagrams.

Figure 1:
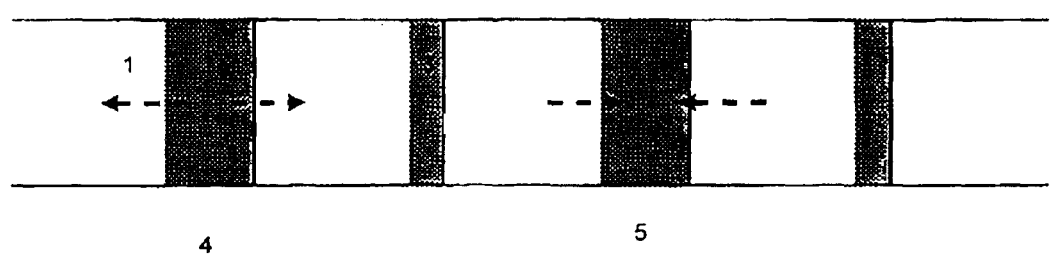
FIG. 1—shows a schematic diagram of a microfabricated device of the invention where compound in fluid phase 2 is allowed to partition into the second fluid 1. At 3 is a barrier plug which is a fluid or gas so as to prevent contamination. Fluids 1 and 2 and barrier 3 flow down the conduit.
Figure 2:
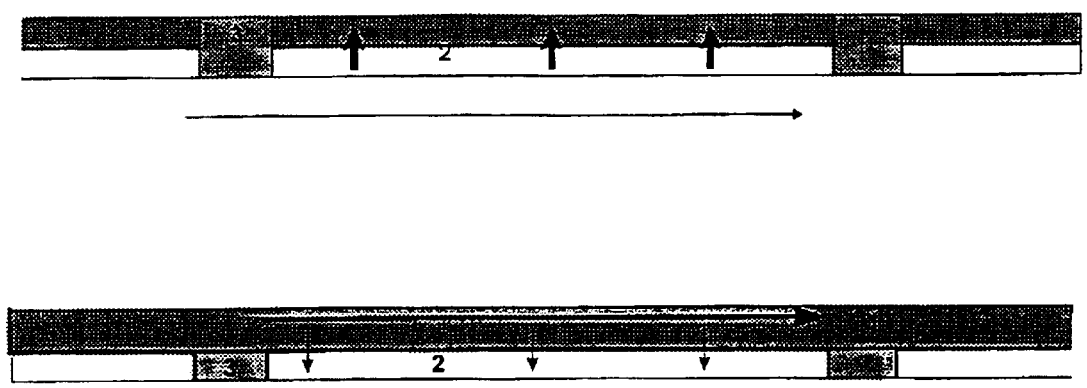
FIG. 2—shows a schematic diagram of a microfabricated device of the invention where compound in fluid 2 is allowed to partition into the second agent 1. At 3 is a barrier plug which is a fluid or a gas so as to prevent contamination. Fluids 1 and 2 and barrier 3 flow down the conduit.
Figure 3:
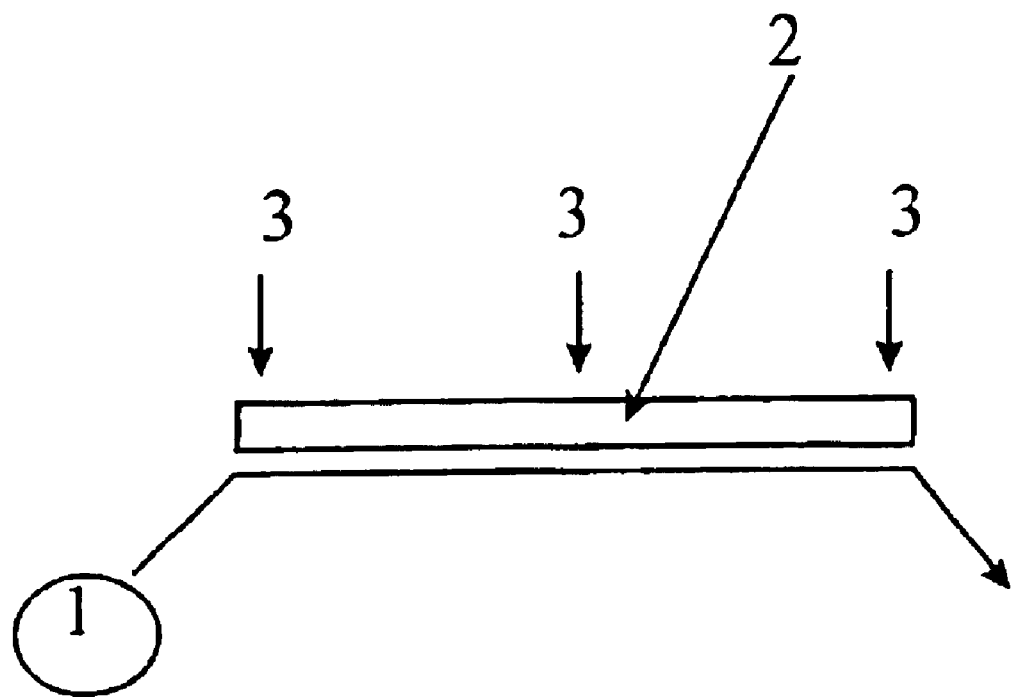
FIG. 3—shows a schematic diagram of a microfabricated device of the invention where compound in a liquid from a compound sample container 1 is brought into contact with the agent 2 and the amount of compound in each partition is measured at suitable detection points FIG. 4—shows a schematic diagram of a microfabricated device for measuring the logP of compound where compound in an aqueous liquid from a compound sample container 1 is brought into contact with the agent 2 flowing from an agent container 4 parallel laminar flow which in this case is an organic solvent. UV light is shone through the microfabricated device and the amount of compound in each partition is measured by MS at suitable detection points 3. As can be seen the ???? flow of the two liquids may be separated at the detection point to more easily measure the amount of compound present in the organic solvent.
Figure 4:
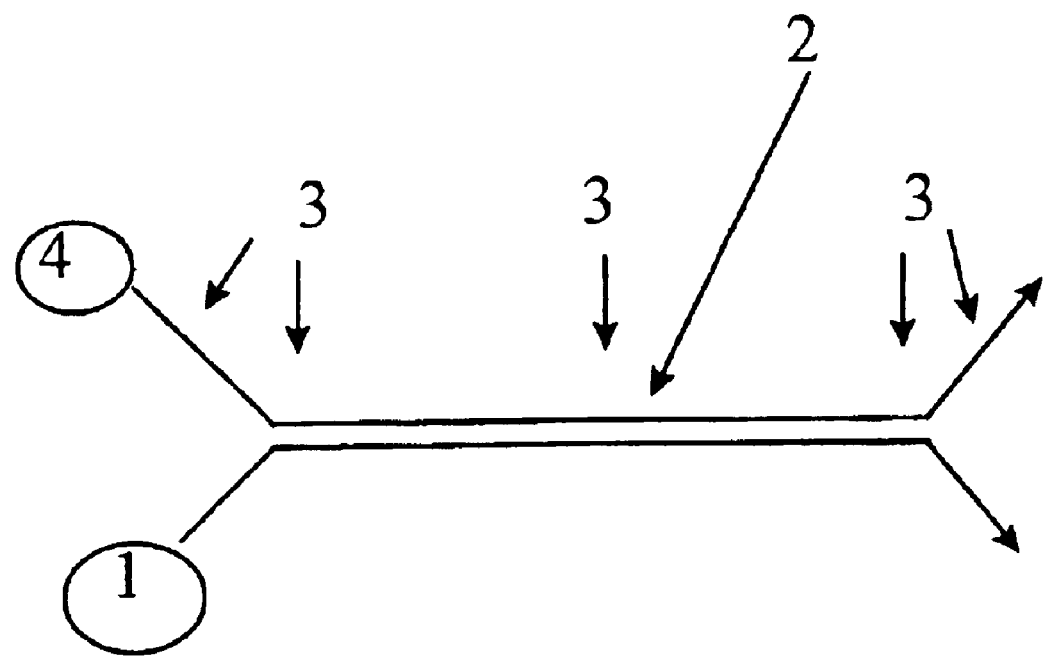

What is claimed is:

1. A system for the determination of at least one physicochemical property of a compound which comprises:
   (i) a microfabricated device having an internal surface defining a first conduit; p1 (ii) a first fluid through said first conduit, said compound being present in the first fluid;
   (iii) a second conduit in said microfabricated device;
   (iv) a second fluid flowing through said second conduit, said second fluid being non-miscible with said first fluid;
   (v) one or more restricted openings being present between the first and second conduits to allow contact between the first and second fluids at the one or more restricted openings via a partition interface formed between the first fluid and the second fluid, the partition interface being formed by contact between the first fluid and the second fluid;
   (vi) a detector for measuring the amount of the compound present within the first fluid or the second fluid or both; wherein presence of compound in either the first fluid or the second fluid or both is measured to determine the physicochemical property due to the partitioning of the compound through the partition interface.

2. A system as claimed in claim 1 which additionally comprises means for moving the first and/or the second fluid through the first and/or second conduits.

3. A system as claimed in claim 1 wherein the detector is an integral part of the microfabricated device.

4. A system according to claim 1 in which the partition interface formed between the first fluid and the second fluid is formed by a third fluid.

5. A method for the measurement of at least one physicochemical property of a compound in a microfabricated device which method comprises:
   (i) providing through an internal surface defining a conduit of the microfabricated device a flow of a first fluid and present within the first fluid is a compound;
   (ii) moving the first fluid through the conduit to bring it into contact with a second fluid via a partition interface formed between the first fluid and the second fluid to allow any partitioning of the compound through the partition interface, said second fluid being non-miscible with said first fluid, the partition interface being formed by contact between non-miscible phases;
   (iii) measuring the amount of the compound present during and/or after partitioning between the first fluid and the second fluid in either the first fluid or the second fluid, or both.

6. A method as claimed in claim 5 wherein the first and second fluids are liquids.

7. A method as claimed in claim 5 wherein a second set of first and second fluids is introduced into the conduit after introduction of a barrier plug.

8. A method according to claim 5 in which the partition interface between the first fluid and the second fluid is formed by a third fluid.

9. A method according to claim 5 in which the physicochemical property is partition coefficient.

10. A method according to claim 5 in which the first fluid flows through a first conduit and the second fluid flows through a second conduit, the first and second fluids contacting via a partion interface at one or more restricted openings between the first and second conduits.

11. A method according to claim 5 in which the first and second fluids are brought into contact as sequential lengths of fluid flowing along the conduit.

12. A method according to claim 11 in which the direction of movement of the flows is periodically reversed.

13. A method according to calm 11 in which the second fluid is firstly inserted, secondly the first fluid is inserted and then thirdly the second fluid is inserted a second time in the conduit.

14. A method according to claim 13 in which the direction of movement of the flows is periodically reversed.

15. A method according to claim 11 in which the first fluid is firstly inserted, secondly the second fluid is inserted and then thirdly the first fluid is inserted a second time in the conduit.

16. A method according to claim 15 in which the direction of movement of the flows is periodically reversed.

* * * * *